United States Patent [19]

Hashizume et al.

[11] Patent Number: 5,190,872
[45] Date of Patent: Mar. 2, 1993

[54] IMMOBILIZED ALCOHOL UTIDASE FOR USE IN AN ALCOHOL MEASURING APPARATUS

[75] Inventors: Yoshio Hashizume, Kakogawa; Akio Kariyone, Kyoto; Ryuzo Hayashi, Higashiosaka; Minako Oka, Sapporo, all of Japan

[73] Assignee: Kanzaki Paper Mfg. Co., Ltd., Tokyo, Japan

[21] Appl. No.: 573,066

[22] Filed: Aug. 27, 1990

[30] Foreign Application Priority Data

Aug. 25, 1989 [JP] Japan .................... 1-219104
Mar. 12, 1990 [JP] Japan .................... 2-61703

[51] Int. Cl.$^5$ .................... C12M 11/14; C12M 1/40; C12Q 1/54; C12Q 1/26
[52] U.S. Cl. .................... 435/176; 435/14; 435/25; 435/175; 435/288; 435/817
[58] Field of Search .................... 435/14, 25, 175, 176, 435/190, 288, 817

[56] References Cited

U.S. PATENT DOCUMENTS

| | | | |
|---|---|---|---|
| 3,669,841 | 4/1972 | Miller | 435/176 |
| 4,540,668 | 9/1985 | Hopkins | 435/190 |
| 4,556,635 | 12/1985 | Hitzman et al. | 435/25 |
| 4,619,898 | 10/1986 | Hopkins | 435/190 |
| 4,900,666 | 2/1990 | Phillips | 435/25 |
| 4,971,901 | 11/1990 | Hayashi et al. | 435/176 |
| 5,037,737 | 8/1991 | Liffmann et al. | 435/817 X |

Primary Examiner—David M. Naff
Attorney, Agent, or Firm—Wenderoth, Lind & Ponack

[57] ABSTRACT

Alcohol oxidase is immobilized by bonding an aminosilane coupling agent to a carrier, bonding a multifunctional aldehyde such as glutaraldehyde to an amino group of the aminosilane, washing the carrier to remove free multifunctional aldehyde and bonding alcohol oxidase to the multifunctional aldehyde bonded to the aminosilane. Washing to remove free multifunctional aldehyde enables immobilizing a one molecule thickness of alcohol oxidase on the carrier since free multifunctional aldehyde is not present to cross-link alcohol oxidase molecules together. A thin layer of alcohol oxidase is advantageous when assaying for alcohol since a thin layer does not retain hydrogen peroxide that can deactivate alcohol oxidase. The carrier preferably contains hydroxyl groups and is porous, and can be a silicate-containing carrier such as diatomaceous earth or fire brick. The immobilized alcohol oxidase is used in a column as part of an apparatus for measuring alcohol or as part of an apparatus containing immobilized glucose oxidase for measuring glucose and alcohol.

8 Claims, 8 Drawing Sheets

IMMOBILIZED ALCOHOL UTIDASE FOR USE IN AN ALCOHOL MEASURING APPARATUS

BACKGROUND OF THE INVENTION

1. Field of Industrial Application

This invention relates to a stable immobilized alcohol oxidase, the method for preparing it and a highly accurate and stable alcohol measuring apparatus using it. The invention further relates to a highly accurate and stable alcohol measuring apparatus which can measure glucose at the same time.

2. Prior Art

Measuring apparatus using an immobilized enzyme are characterized in convenience, expediency and substrate specificity and are used in various fields such as clinical analysis, food analysis, and environmental instrumentation.

In the progress of the development of such a measuring apparatus using an immobilized enzyme, alcohol, particularly, ethanol analysis has been in particular demand in the fields of such as food, fermentation, and clinical field. However, with respect to the enzyme used for measurement of alcohol, none of sufficient stability has yet been obtained.

As an enzyme which can be used for alcohol measurement, there are known those such as alcohol dehydrogenase (EC.1.1.1. 1) and alcohol oxidase (EC.1. 1. 3. 13).

However, the alcohol dehydrogenase requires NAD (nicotinamide adenine dinucleotide) as a coenzyme, leading to higher cost of reagents used in analysis, and the stability of the enzyme is low. This enzyme is limited in used to measurement in a solution.

On the other hand, the alcohol oxidase is known to have been used in measurement after being immobilized.

However, such conventional immobilized alcohol oxidase is relatively low in activity and the stability is unsatisfactory in practical use.

U.S. Pat. No. 4,556,635, for example, describes a method for measuring alcohol concentration in water immiscible organic systems, but the preferable temperature is about 25° C. accordingly, this enzyme is easily deactivated at relatively high temperature. Thus, using a conventional immobilization method, this measuring method has a substantial limitation in the practical use of alcohol oxidase.

U.S. Pat. No. 4,900,666 discloses a measuring method and test device using alcohol oxidase. However, as described in this specification, the alcohol oxidase is degenerated very readily, and various stabilizers have been studied, but those having sufficient effect for application to a measuring apparatus using immobilized enzyme have not yet been obtained.

In addition, these measuring apparatuses using conventional immobilized enzyme, have a defect, that is, after the high concentration alcohol exceeding the measuring range has been measured, response to the low concentration alcohol becomes smaller, that is, the sensitivity is varied.

In the field of fermentation and foods, the necessity of simultaneous measurement of glucose, a sweetener or raw material, and alcohol, a product or main component, is high. However, use of the conventional unstable immobilized alcohol oxidase could not afford development of a satisfactory simultaneous measuring apparatus.

Accordingly, it is an object of the present invention to provide a stable immobilized alcohol oxidase and a high-accuracy and stable alcohol measuring apparatus using it, particularly, to provide an alcohol measuring apparatus with excellent stability at room temperature or higher and of no sensitivity variation after measurement of the high concentration alcohol.

Another object of the invention is to provide a high-accuracy and stable alcohol measuring apparatus which can measure glucose at the same time.

These and other objects of the invention will be explicit from the following description of the invention.

SUMMARY OF THE INVENTION

To attain the above objects, the invention provides
An immobilized alcohol oxidase produced by at least following steps of:

a) boning an aminosilane coupling agent to the surface of a carrier, b) bonding a multifunctional aldehyde to an amino group formed on the surface of said carrier by said aminosilane coupling treatment, and c) bonding an alcohol oxidase to said multifunctional aldehyde bonded to said amino group.

In a preferred embodiment of the invention, said steps contain additionally the following step of:

d) washing said carrier to remove said multifunctional aldehyde in a free state after said step b) and before said step c).

In another preferred embodiment of the invention, said carrier possesses hydroxyl group.

In still another preferred embodiment, said carrier contains silicate.

Preferably, said carrier containing silicate is a diatomaceous earth or a fire brick obtained by high temperature treatment of diatomaceous earth containing material.

In a preferred embodiment of the invention, said alcohol oxidase is immobilized on said carrier having porous surface, in the form of a thin layer having a thickness corresponding to approximately a thickness of one molecule of alcohol oxidase.

The invention also provides a flow type alcohol measuring apparatus comprising a column filled with an immobilized alcohol oxidase, and a hydrogen peroxide electrode provided downstream of said column, wherein said immobilized alcohol oxidase is produced by at least the following steps of:

a) bonding an aminosilane coupling agent to the surface of a carrier, b) bonding a multifunctional aldehyde to an amino group formed on the surface of said carrier by said aminosilane coupling treatment, and c) bonding an alcohol oxidase to said multifunctional aldehyde bonded to said amino group.

In a preferred embodiment of the invention, said flow type measuring apparatus additionally comprises an immobilized enzyme electrode for detecting glucose concentration provided upstream of said column or downstream of said hydrogen peroxide electrode.

The invention also provides a process for preparing an immobilized alcohol oxidase comprising the steps of:

a) bonding an aminosilane coupling agent to the surface of a carrier, b) bonding a multifunctional aldehyde to an amino group formed on the surface of said carrier by said aminosilane coupling treatment, and c) bonding an alcohol oxidase to said multifunctional aldehyde bonded to said amino group.

According to the invention, an immobilized enzyme having higher heat resistance and longer life is obtained.

According to the invention the alcohol oxidase is immobilized stably so that an excellent alcohol measuring apparatus is easily prepared. Particularly, an alcohol measuring apparatus with higher heat resistance and with little variation in sensitivity even after the measurement of high concentration alcohol can be prepared.

According to the invention, an alcohol and glucose measuring apparatus of high-accuracy and stability is easily achieved.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

While studying the characteristics of the alcohol oxidase and trying various immobilizing methods, the inventors have noted from the following experimental results that in the measurement using the immobilized alcohol oxidase electrode, after a measurement of a high-concentration alcohol solution the response to a low-concentration alcohol solution sample becomes smaller.

EXPERIMENTAL RESULTS

Alcohol oxidase was mixed with bovine serum albumin and further with glutaraldehyde and placed on a platinum electrode to give an immobilized enzyme electrode. Measurement was made using a three electrode system using this enzyme electrode as a working electrode, a counter electrode of platinum wire and an Ag/AgCl reference electrode. In a sodium phosphate buffer solution of pH 7.5, a voltage of +0.6 V against the Ag/AgCl reference electrode was applied to the working electrode. The measuring temperature was room temperature (25° C.). First the sensitivity was recorded with ethanol equivalent to 0.1–1 mM added to the buffer solution. In this concentration range, the output current was proportional to the concentration of ethanol added. Then, ethanol equivalent to 1M was added and left to stand for one minute, and the buffer solution was replaced by new one, and the sensitivity was checked again with ethanol of low concentration. This showed that the sensitivity was decreased to about 50%.

However, the enzyme electrode thus exposed to ethanol of such a high concentration restores its sensitivity to about 90% of the initial value when allowed to leave about 1 hr in buffer solution.

Then, the sensitivity was measured one minute after an addition of hydrogen peroxide equivalent to 10 mM. This showed a sensitivity decrease and then sensitivity restoring with time, similar to the case of exposure to the high concentration alcohol.

The above experimental results show that the alcohol oxidase is inhibited by $H_2O_2$ produced, and aldehyde which is also produced by the catalytic reaction of the alcohol oxidase can cause deactivation of the alcohol oxidase.

To prevent deactivation by such products, hydrogen peroxide or the like should be removed from the vicinity of the immobilized alcohol oxidase as quick as possible. As the results of various investigations, the inventors have completed the invention.

In the invention an alcohol oxidase is preferably immobilized on a carrier in the form of a thin layer having a thickness corresponding to approximately a thickness of one molecule of the alcohol oxidase, namely a single layer of about 20–300 Å in thickness corresponding to a diameter of the alcohol oxidase having molecular weight of about 200,000.

Here, "a single layer" of the alcohol oxidase means that the alcohol oxidase molecules are not arranged in multilayers on the carrier surface.

Thus, the thickness of the layer of an immobilized alcohol oxidase is preferably about 20–300 Å, corresponding to the diameter of the alcohol oxidase Since the alcohol oxidase is thus arranged in a single layer, reaction products are removed from the enzyme layer readily, and the deactivation of the alcohol oxidase by the reaction products can be prevented.

The alcohol oxidase used here is an enzyme produced by such microorganisms as Basidiomycete and yeast, and contained, particularly in large quantities in peroxisome of methanol-utilizing yeast.

Examples of the carrier are silica gel, glass beads, sand, alumina, zirconia, ceramics, carbon, active carbon, molecular sieve, titania, tannin, silicone rubber, acid clay, cellulose, agarose, dextran, chitin, collagen, amino acid based polymer, polystyrene resin, polyacrylamide, polyvinyl alcohol, nylon, and ion-exchange resin diatomaceous earth based silicate such as diatomaceous earth and fire brick. Among these, carriers possessing hydroxyl groups are preferably used, because they easily react with coupling reagents, and having a porous surface are preferably used, too. Further among these, carriers having relatively large pores with the specific surface area of 2–9 $m^2/g$ is preferably used, and especially silicate is preferably used. The carrier used is more preferably a diatomaceous earth or a fire brick obtained by high temperature treatment of diatomaceous earth containing material.

The alcohol oxidase can be immobilized as follows. For example, the enzyme is immobilized with the carrier as it is, or with a functional group which is reactive with the enzyme, or with the functional group of the activated carrier. To introduce a functional group, the diazo method, peptide method, alkylation method, or covalent bonding method using a cross-linking reagent (glutaraldehyde, hexamethylene diisocyanate, etc.) can be used.

To get an alcohol oxidase immobilized stably and having longer life, the alcohol oxidase is immobilized with following steps.

That is, an immobilized alcohol oxidase produced by at least following steps of:

a) bonding an aminosilane coupling agent to the surface of a carrier, b) bonding a multifunctional aldehyde to an amino group formed on the surface of said carrier by said aminosilane coupling treatment, and c) bonding an alcohol oxidase to said multifunctional aldehyde bonded to said amino group.

Figure 1A:
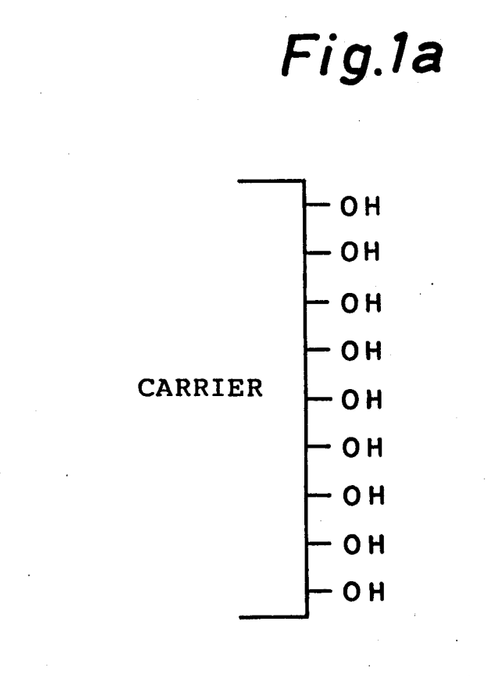
FIGS. 1a–1d are a diagram showing an immobilized alcohol oxidase, formed in an embodiment of Example 1
Figure 1B:
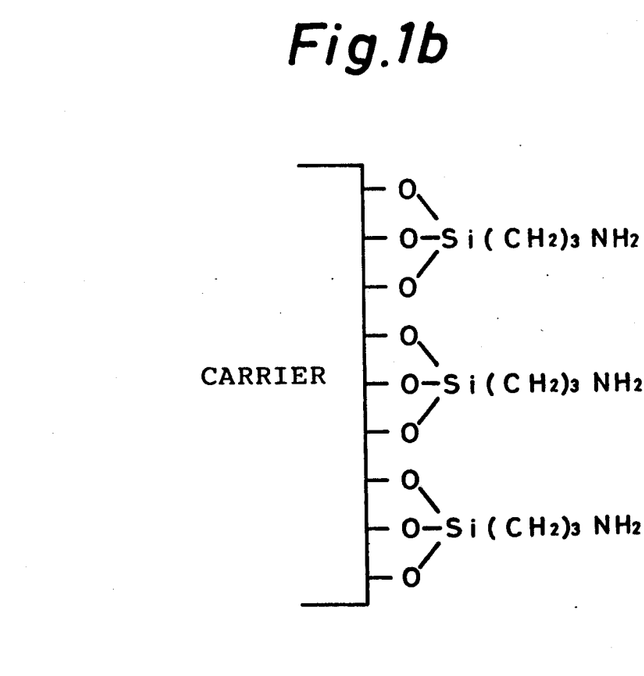

According to this method, first:

(1) There is no possibility of multiple layers formation in the step of providing amino group layer (silane coupling agent layer) on the carrier surface, (See FIG. 1b)

Figure 1C:
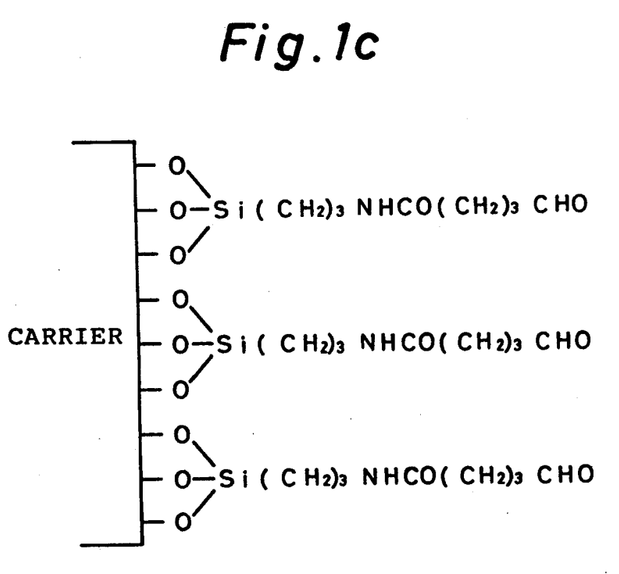

(2) There is no possibility of multiple layers formation also in the step of reacting the multifunctional aldehyde such as glutaraldehyde (See FIG. 1c)

(3) Since the cross-linking reaction is performed with the alcohol oxidase brought in contact preferably after free excessive cross linking agent has been removed, the alcohol oxidase molecules are not cross linked being arranged into multilayers. That is, when the alcohol oxidase is immobilized by use of the cross-linking agent, a plurality of crosslinking position on the carrier surface may react with an alcohol oxidase, but an alcohol oxidase is not piled on another alcohol oxidase (See FIG. 1d).

For these reasons, a thin layer of alcohol oxidase can be formed on the carrier surface and can effectively prevent the retention of hydrogen peroxide, etc. in the interior of the enzyme layer, thus leading to prevent deactivation of the alcohol oxidase by the reaction products.

The amount of enzyme immobilized on the carrier is estimated by the enzyme specific activity per unit surface area of the carrier. In the case of the present invention, the activity of alcohol oxidase is preferably 10–1000 IU (International Unit)/m². To form a thin layer of immobilized enzyme, an excellent immobilized enzyme both in sensitivity and life expectancy is obtained with such amount of immobilized enzyme.

According to the preferred embodiment: the use of the diatomaceous earth based silicate carrier makes it possible to immobilize enzyme on the carrier having fairly coarse pores on the surface. Therefore, both the alcohol, the substrate, and hydrogen peroxide, the product, can be removed without remaining in the pores. Thus, the inhibition to the alcohol oxidase is prevented.

The diatomaceous earth based silicate carrier is exemplified by natural diatomaceous earth and its granulate, and fire brick obtained by high temperature treatment of diatomaceous earth. Fire brick also obtained by high temperature treatment of the material mixed with about 0.1–10% of flux, such as, sodium carbonate, magnesium carbonate, calcium carbonate and so on, in addition to diatomaceous earth. Any of these is an aggregate of primary particles of about 1 μm, having relatively coarse pores with specific surface area of 2–9 m²/g. This value shows that the pores (0.1 μm or more) verified by a scanning electron microscope are main pores. A similar carrier is silica gel but the silica gel has a finer pore diameter (specific surface area 30–70 m²/g), so the diatomaceous earth based silicate carrier is superior in the effect than silica gel.

The investigation of the life of the alcohol oxidase immobilized on various carriers, including diatomaceous earth based silicate carrier and silica gel, having various pore diameters, showed that those immobilized on a diatomaceous earth based silicate carrier a the most excellent in heat resistance and long life.

The reason for these excellent properties is considered to be done to the quick removal of the product based on the difference of the pore diameter, and there is also the possibility that the trace amounts of calcium and iron contained in the diatomaceous earth based silicate carrier have a stabilizing effect or that the silane coupling agent is relatively firmly bonded so as to decrease the loosening of the enzyme form the carrier surface.

The aminosilane coupling treatment is proceeded by use of a silane coupling agent such as γ-aminopropyltriethoxysilane, 4-amino-butyldimethylmethoxysilane, 4-aminobutyltriethoxysilane, and generally is effected by immersing the carrier in a silane coupling agent solution in dry benzene or anhydrous toluene. Aminotitanium coupling agent can be used instead of aminosilane coupling agent.

The multifunctional aldehyde is exemplified by glutaraldehyde and glyoxal. In practical use, bifunctional aldehyde, particularly, glutaraldehyde, a mild crosslinking agent, is preferable.

The alcohol oxidase is deactivated even by glutaraldehyde, a relatively mild crosslinking agent. In the above method, however, since the alcohol oxidase is immobilized by contact after the silane coupling agent and the multifunctional aldehyde have been bonded to the carrier, the enzyme is not deactivated by unnecessary modification by excess aldehyde Thus, such carrier and immobilizing method give an immobilized alcohol oxidase having the excellent heat resistance and long life.

The use of alkylation method or diazo method as an immobilizing method gives effect similar to the above. However, since the reagents used in these methods have relatively low reactivity, the quantity of enzyme immobilized on the carrier can be decreased. Accordingly the sensitivity can be decreased, thus, the above method is preferable.

The immobilized alcohol oxidase according to the invention is used also as a reactor for aldehyde production and for removal of alcohol, but used in particular preferably for an alcohol measuring apparatus.

As an alcohol measuring apparatus, a column reactor system is preferable for preventing inhibition by products and for attaining long life.

As a measuring apparatus using the immobilized enzyme, an amperometric measuring apparatus is available. This apparatus measures the increase or decrease of the electrode active substance caused by the enzyme reaction as the variation of the current output from the immobilized enzyme electrode impressed with a constant voltage. Having sensitivity easily raised and excellent stability, this apparatus is used in various electrodes, devices, and methods. Representative examples of amperometric analysis method include those by oxygen electrode and by hydrogen peroxide electrode, and the method using hydrogen peroxide electrode is better in response speed and S/N ratio.

Accordingly, the invention is a flow type alcohol measuring apparatus characterized in that a column filled with the immobilized alcohol oxidase is provided and a hydrogen peroxide electrode is arranged downstream of the column.

With a combination of this measuring system comprising the immobilized alcohol oxidase filled column and hydrogen peroxide electrode, together with a glucose measuring electrode, a simultaneous alcohol and glucose measuring apparatus for very quick and high accuracy measurement can be prepared.

Accordingly, the invention also provides a flow type alcohol and glucose measuring apparatus characterized in that a column filled with the immobilized alcohol oxidase is provided, a hydrogen peroxide electrode arranged downstream of the column and an electrode for measuring glucose is provided in series.

The electrode for measuring glucose is, for example, a hydrogen peroxide electrode or oxygen electrode having immobilized glucose oxidase or pyranose oxidase membrane, and the hydrogen peroxide electrode is superior as mentioned before.

The electrode for measuring glucose can be arranged either upstream of the immobilized alcohol oxidase column or downstream of the hydrogen peroxide electrode, but in a measurement of a sample containing high-concentration alcohol and glucose, remarkable consumption of dissolved oxygen and formation of hydrogen peroxide occur in the immobilizing alcohol oxydase column. Therefore, the glucose measuring electrode is preferably arranged upstream of the immobilized alcohol oxidase column. It is of course possible to make up a double flow path type flow measuring apparatus, but it is preferable for measurement of higher accuracy to configure a series arrangement type apparatus, since in a double flow path type the flow dividing ratio for division of injected sample flow can be largely varies due to stained piping, etc.

It is also possible to make up various simultaneous measuring units by using together an immobilized alcohol oxidase electrode other than a glucose measuring electrode. For example, a simultaneous measuring apparatus of saccharides such as cane sugar, fructose, and maltose, and organic acids such as lactic acid, and amino acids such as glutamic acid. Further, a pH electrode and ion-selective electrode such as a sodium electrode and ammonia electrode can be used.

EXAMPLES

The invention will now be more particularly described by way of examples, but it should be noted that the invention is not limited to these. Here, "%" represents "% by weight".

EXAMPLE 1

(1) Preparation of Electrode

The side of a platinum wire of 2 mm in diameter was coated with heat-shrinkable Teflon ® and its end was finished smoothly by file and No. 1500 emery paper. Using this platinum wire as the working electrode, a 1-cm square platinum plate as the counter electrode, and a saturated calomel electrode (hereinafter referred to as SCE) as the reference electrode, electrolysis was performed in 0.1M sulfuric acid at +2.0 V for 10 minutes. After thorough washing, the platinum wire was dried at 40° C. for 10 minutes, immersed in a 10% γ-aminopropyl triethoxysilane solution in anhydrous toluene, and washed.

20 mg of bovine serum albumin (Fraction V supplied by Sigma Co.) was dissolved in 1 ml of distilled water and then glutaraldehyde was added into it to make the resulting solution to contain 0.2% of glutaraldehyde. 5 μl of this mixed solution was quickly put on the platinum wire prepared above, and dried and cured at 40° C. for 15 minutes to form a hydrogen peroxide selectively permeable membrane. This was used as the hydrogen peroxide electrode.

(2) Preparation of Immobilized Enzyme Column

Figure 1D:
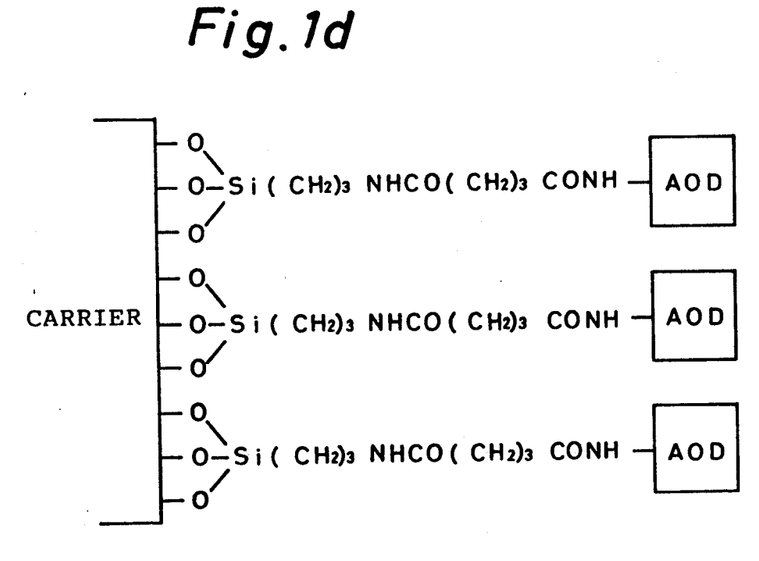

FIGS. 1c–1d show a model of the immobilization of alcohol oxidase. As the carrier fire brick, diatomaceous earth based silicate, carrier was used. A quantity of 150 mg of fire brick (60–80 mesh classification) was thoroughly dried and allowed to stand for 1 hr with an addition of 1 ml of 10% γ-aminopropyl triethoxysilane solution in anhydrous toluene. After thoroughly washing this silane coupling agent with toluene and methanol, this carrier was dried at 120° C. for 2 hr (FIG. 1b). After being allowed to cool, it was allowed to stand for 1 hr with an addition of 0.5 ml of 5% aqueous glutaraldehyde solution. This carrier was thoroughly washed with water. Finally it was washed with sodium phosphate buffer solution of pH 7.0 and the buffer solution was removed as far as possible (FIG. 1c).

To this amino silane coupling treated carrier, 50 μl of enzyme solution of alcohol oxidase (liquid enzyme specimen derived from *Pichia pastolis*, supplied by Sigma Co.) diluted 10 times with sodium phosphate buffer solution at pH 7.0 was added and left to stand for 1 hr under ice cooling. Then, it was thoroughly washed with the buffer solution (FIG. 1d). Specific surface area of used fire brick was 0.3 m$^2$, activity of immobilized alcohol oxidase was 62.5 IU, accordingly, the specific activity of alcohol oxidase was 208 IU/m$^2$. Thus, a 20–300 Å thick single layer was formed with nearly every alcohol oxidase molecule (shown by AOD in FIG. 1d) immobilized one by one. This enzyme immobilized carrier was filled in a polytetrafluoro ethylene resin tube of outer diameter 3 mm, inner diameter 2 mm, and length 10 cm.

(3) Measuring Apparatus

Figure 2:
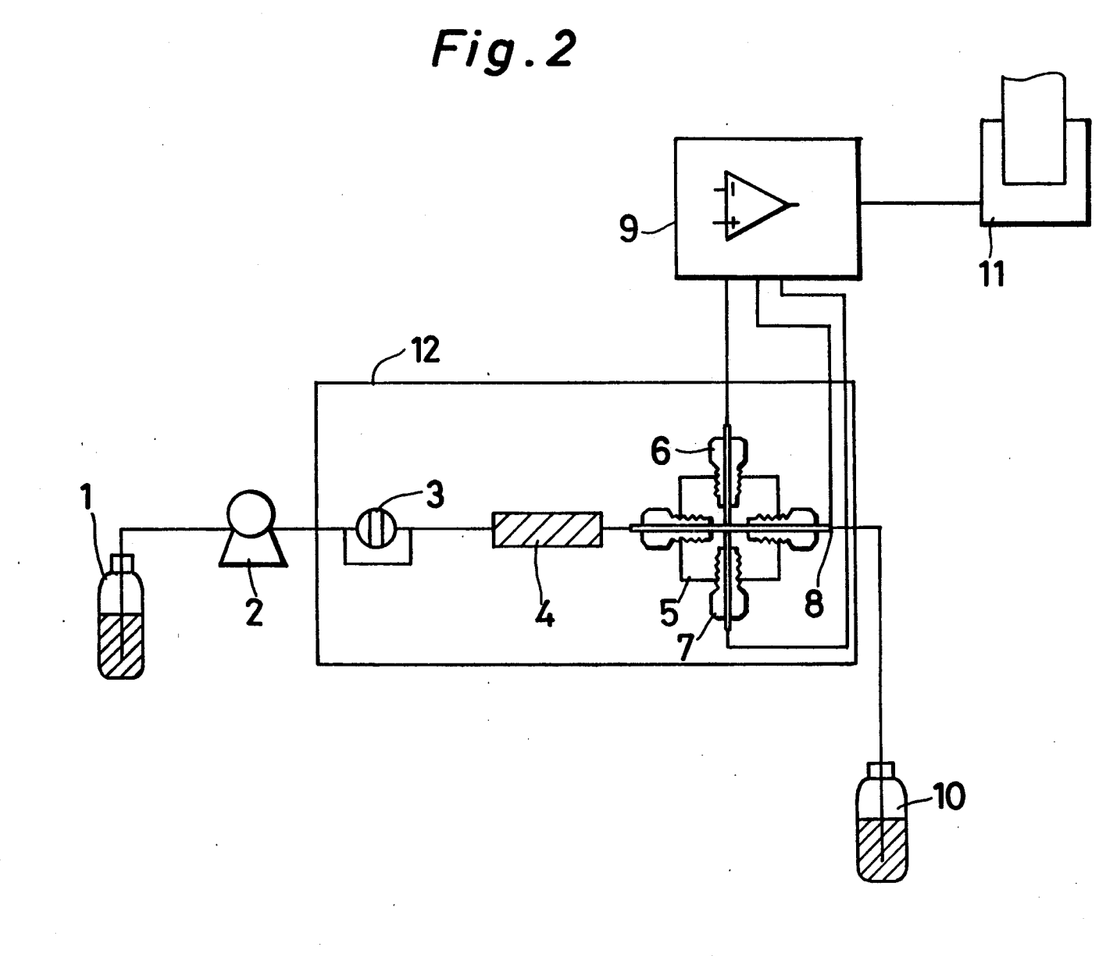
FIG. 2 is a system diagram of the flow type measuring apparatus used in Examples 1–3.

A flow type measuring apparatus shown in FIG. 2 was used. This flow type measuring apparatus comprised an injector 3 for high-speed liquid chromatography (7125 type injector made by Rheodyne Co.) and the measuring cell 5 with stainless steel piping containing the hydrogen peroxide electrode 6, the Ag/AgCl electrode 7 as a reference electrode and the counter electrode 8. The injector 3, immobilized enzyme column 4, and measuring cell 5 were connected in this order with Teflon ® piping of inner diameter 0.5 mm and length 0.5 m. The internal volume of the measuring cell 5 was 40 μl, and the hydrogen peroxide electrode 6 and the Ag/AgCl electrode 7 were arranged opposite to each other through the pipe of buffer solution. The hydrogen peroxide electrode 6 was impressed with a voltage of +0.6 V against Ag/AgCl electrode 7 by potentiostat 9. The injector 3, immobilized enzyme column 4, and measuring cell 5 were installed in a thermostat 12. The temperature in the thermostat 12 was held to 37°±0.2° C. For pumping the buffer solution 1, a pump 2 for high-speed liquid chromatography was used and the buffer solution was pumped at a flow rate of 1.0 ml/min. The buffer solution was the solution of 100 mM sodium phosphate (pH 7.0) containing 1 mM sodium azide.

The buffer solution used in measurement was caught in a waste reservoir 10. Measurements were recorded by a recorder 11.

(4) Measuring Method

The column containing carrier immediately after immobilization was mounted on the measuring apparatus, and after the constant temperature of thermostat reached to equilibrium, 10 μl of 100 mM ethanol solution was injected. The sensitivity at that time was recorded. The thermostat was held at 37° C. for 8 hr, and the ethanol solutions of 30 samples were measured in one hour. During the night, the pumping was stopped and the ambient temperature of the column was held to 30° C.

Thus, in daytime the measurement at 37° C. was continued for 8 hr and during the night the column was left to stand in the environment of 30° C., and the sensitivity to the 100 mM ethanol solution was recorded every day. Making the sensitivity first recorded immediately after the immobilization 100%, the change of sensitivity thereafter was shown in FIG. 3 (o mark). For several days after the start of recording, the increase of the sensitivity was observed and stabilized thereafter. This increase of the sensitivity was due to the deactivation of the catalase which was included in alcohol oxidase as an impurity. That is, the hydrogen peroxide which is produced simultaneously with the oxidation of alcohol is decomposed by catalase in the early measurements, but because of the deactivation of catalase in a few days, hydrogen peroxide is quantitatively eluted from the column and detected.

Figure 3:
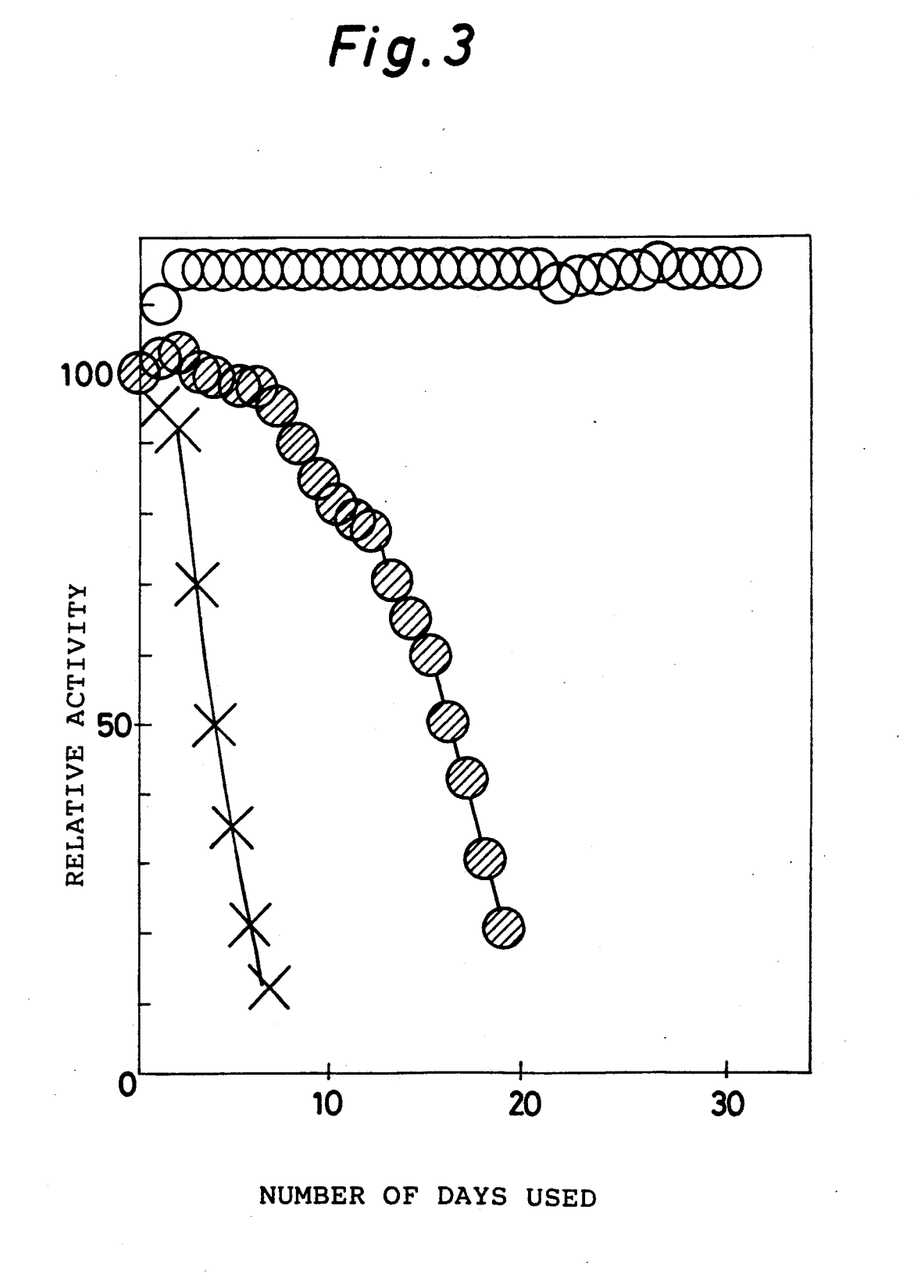
FIG. 3 is a graph showing the results of measurement of Example 1 (demonstrated by the mark ⦿), Reference 1 (demonstrated by the mark φ), and Reference 2 (demonstrated by the x).

As shown by FIG. 3, the immobilized alcohol oxidase prepared according to the invention was very stable in spite of using 37° C. and reserving 37° C. and showing no deterioration of the activity even after a month.

To the apparatus provided with the immobilized enzyme, ethanol solutions of 100 mM and 1M were alternately injected. In the case of 1M solution, the output value was saturated and could not be determined, but gave no influence on the measurement of 100 mM ethanol solution injected immediately after, and the sensitivity variation was not observed.

REFERENCE 1

(1) Preparation of Electrode

A hydrogen peroxide electrode same as in Example 1 was prepared and used.

(2) Preparation of Immobilized Enzyme Column 150 mg of fire brick (60–80 mesh classification) with an addition of 50 μl of alcohol oxidase (liquid enzyme specimen derived from *Pichia pastolis*, supplied by Sigma Co.), 50 mg of bovine serum alubumin, and 0.95 ml of sodium phosphate buffer solution of pH 7.0, and further with glutaraldehyde to make the resulting concentration thereof 0.2%, was left to stand for 5 hr in a refrigerator to dryness. After being left alone, it was thoroughly washed with buffer solution. This enzyme immobilized carrier was filled into a polytetrafluoro ethylene resin tube of outer diameter 3 mm, inner diameter 2 mm, and length 10 cm. Immobilized by this method, a relatively thick layer of the immobilized enzyme of several to several tens microns thickness was formed in contrast to 20–300 Å of the immobilized enzyme layer according to the invention.

(3) Measuring Apparatus

The same apparatus as in Example 1 was used except that the above column was used as the immobilized enzyme column.

(4) Measuring Method

The life of the immobilized enzyme was evaluated by the same measuring method as in Example 1. The results were shown in FIG. 3 (● mark).

As obvious from FIG. 3, the immobilized alcohol oxidase prepared by the method in Example 1 was very stable, while when the immobilized enzyme column obtained by the method in Reference 1 was used, the sensitivity began to drop after one week, and it dropped to about 20% of the initial sensitivity after 19 days.

When the immobilized enzyme column in Reference 1 was used, the time until the hydrogen peroxide detecting peak finishes became about 1.5 times as long as that of Example 1, it means that the retention time of hydrogen peroxide in the immobilized enzyme layer is extended as much.

Like in Example 1, ethanol solutions of 100 mM and 1M were alternately injected into an apparatus provided with this immobilized enzyme column. The measurements of the 100 mM ethanol solution injected after 1M solution were decreased to about 60%, showing a large influence of 1M solution measurement.

REFERENCE 2

(1) Preparation of Electrode

A platinum wire of 2 mm in diameter was coated with heat shrinkable Teflon® and its end was finished smoothly by file and No. 1500 emery paper. Using this platinum wire as the working electrode, a 1-cm square platinum plate as the counter electrode, and a SCE as the reference electrode, electrysis was performed in 0.1M sulfuric acid at +2.0 V for 10 minutes. After thorough washing, the platinum wire was dried at 40° C. for 10 minutes, immersed in a 10% γ-aminopropyl triethoxysilane solution in anhydrous toluene, and washed.

20 mg of bovine serum albumin (Fraction V supplied by Sigma Co.) was dissolved in 1 ml of distilled water and then glutaraldehyde is added into it to make the resulting solution to contain 0.2% of glutaraldehyde. 5 μl of this mixed solution was quickly put on the platinum wire prepared above, and dried and cured at 40° C. for 15 minutes. This was used as the hydrogen peroxide electrode.

Further, to 50 μl of alcohol oxidase (an enzyme specimen same as that in Example 1) and 50 mg of bovine serum albumin, 0.95 ml of 100 mM sodium phosphorate buffer solution (pH 7.0) was added, and glutaraldehyde was further added to make the resulting mixed solution to contain 0.2% of glutaraldehyde. On the bovine serum albumin membrane of the hydrogen peroxide electrode, 5 μl of this mixed solution was put and dried at 40° C. for 15 minutes to get an enzyme electrode for alcohol measurement. Surface area of the electrode was $3.14 \times 10^{-6}$ $m^2$, activity of immobilized alcohol oxidase was 0.313 IU, accordingly, the specific activity of alcohol oxidase was 99500 $IU/m^2$. The activity was extremely high in comparison with the immobilized enzyme on the carrier in Example 1, 2, 3. This enzyme electrode was used in the following experiment.

(2) Measuring Apparatus

The same apparatus as in Example 1 was used except that the enzyme electrode was used instead of the hydrogen peroxide electrode and the immobilized enzyme column was removed.

(3) Measuring Method

The life was evaluated in the same manner as in Example 1. The results are shown in FIG. 3 (x mark).

In the case of enzyme electrode, a remarkable sensitivity drop was observed from 3 days after the start of measurement, and in 5 days the sensitivity dropped to about 35%. It is obvious that the ability is inferior to that of the column reactor system in Example 1.

EXAMPLE 2

(1) Preparation of Electrode

The hydrogen peroxide electrode was prepared by the same method as in Example 1.

(2) Preparation of Immobilized enzyme Column 200 mg of silica gel (80–100 mesh classification) was thoroughly dried and with an addition of 1 ml of 10% γ-aminopropyl triethoxysilane solution in anhydrous toluene, was allowed to stand for 1 hr. After thoroughly washing this silane coupling agent with toluene and methanol, this carrier was dried at 120° C. for 4 hr. After being allowed to cool, with an addition of 0.5 ml of aqueous 5% glutaraldehyde solution, it was allowed to stand for 1 hr at room temperature. This carrier was thoroughly washed with water. Finally it was washed with sodium phosphate buffer solution of pH 7.0 and the buffer solution was removed as far as possible.

50 μl of alcohol oxidase solution (liquid enzyme specimen derived from *Pichia pastolis*, supplied by Sigma Co.) was diluted by 10 times with sodium phosphate buffer solution at pH 7.0 and added to this aminosilane coupled carrier, and left to stand for 1 hr under ice cooling. Then, it was thoroughly washed with buffer solution. Surface area of used silica gel was 24 m$^2$, activity of immobilized alcohol oxidase was 62.5 IU. Accordingly, the specific activity of alcohol oxidase was 2.6 IU/m$^2$. This alcohol oxidase immobilized carrier was filled in a polytetrafluoro ethylene resin tube of outer diameter 3 mm, inner diameter 2 mm, and length 10 cm.

(3) Measuring Apparatus

The same apparatus as in Example 1 was used.

(4) Measuring Method

The life of the the immobilized enzyme was checked by the same method as in Example 1.

In daytime, the measurement at 37° C. was continued for 8 hr and during the night the column was left to stand in the environment of 30° C. The sensitivity to the 100 mM ethanol solution was recorded everyday. The change of sensitivity thereafter was shown in FIG. 4, making the sensitivity recorded first immediately after the immobilization 100%. For several days after the start of recording the increase of sensitivity was observed and then stabilized thereafter like in the case of Example 1.

Figure 4:
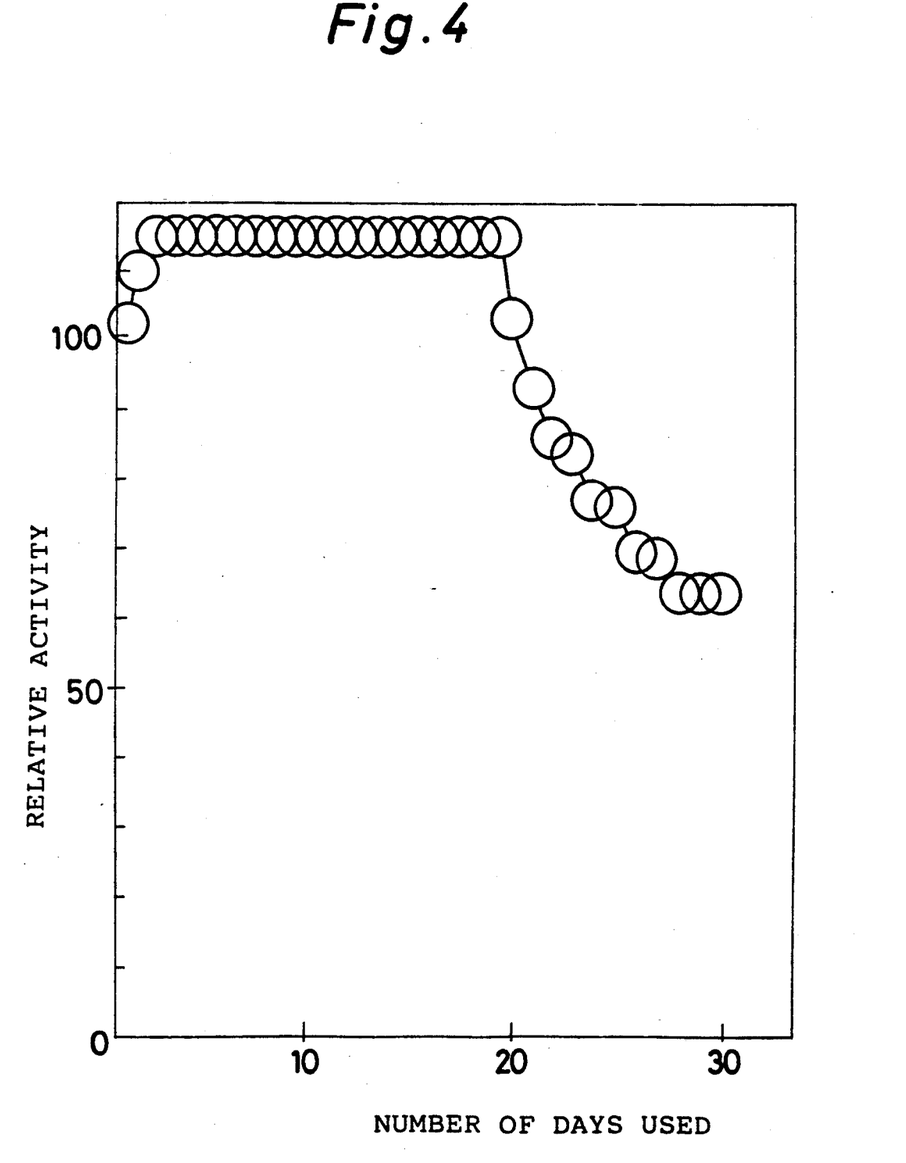
FIG. 4 is a graph showing the results of measurement Example 2.

As obvious from FIG. 4, the immobilized alcohol oxidase prepared according to the embodiment of the invention was very stable, showing no deterioration of the activity for about 3 weeks. This means that the durability is very much improved in comparison with Reference 1 and Reference 2. However, the pore of silica gel is finer than that of fire brick, and this tends to be delayed the eluation of hydrogen peroxide, and for this reason hydrogen peroxide is apt to stay near the enzyme longer than in the case of the fire brick. This may explain somewhat shorter life of the alcohol oxidase.

To this apparatus provided with the immobilized enzyme column, ethanol solutions of 100 mM and 1M were alterately injected. In the case of 1M solution, the output value was saturated and could not be determined, but gave no influence on the measurement of 100 mM ethanol solution injected immediately after.

EXAMPLE 3

(1) Preparation of Electrode

The hydrogen peroxide electrode was prepared by the same method as in Example 1.

(2) Preparation of Immobilized Enzyme Column 150 mg of diatomaceous earth (Celite 545, 40–60 mesh classification, supplied by Kishida Chemical Ltd.), diatomaceous earth based silicate carrier, was thoroughly dried and allowed to stand for 1 hr with an addition of 1 ml of 10% γ-aminopropyl triethoxysilane solution in anhydrous toluene. After thoroughly washing this silane coupling agent with toluene and methanol, this carrier was dried at 120° C. for 4 hr. After being allowed to cool, the carrier was allowed to stand for 1 hr with an addition of 0.5 ml of 5% aqueous glutaraldehyde solution at room temperature. This carrier was thoroughly washed with water and finally washed with sodium phosphate buffer solution of pH 7.0 and the buffer solution was removed as far as possible.

50 μl of enzyme solution of alcohol oxidase (liquid enzyme specimen derived from *Pichia pastolis*, supplied by Sigma Co.) was diluted by 10 times with sodium phosphate buffer solution of pH 7, and was added to this aminosilane coupling treated carrier and left to stand for 1 hr under ice cooling. Then, it was thoroughly washed with the buffer solution. Surface area of used diatomaceous earth was 0.3 m$^2$, activity of immobilized alcohol oxidase was 62.5 IU. Accordingly, the specific activity of alcohol oxidase was 208 IU/m$^2$. This enzyme immobilized carrier was filled in a polytetrafluoro ethylene resin tube of outer diameter 3 mm, inner diameter 2 mm, and length 10 cm.

(3) Measuring Apparatus

The apparatus same as in Example 1 was used.

(4) Measuring Method

The life of the immobilized enzyme was checked by the same method as in Example 1.

In daytime, the measurement at 37° C. was continued for 8 hr and during the night the column was left to stand in the environment of 30° C. The sensitivity to 100 mM ethanol solution was recorded every day. The change of sensitivity thereafter was shown in FIG. 5, making the sensitivity recorded first immediately after the immobilization 100%. For several days after the start of recording, the increase of sensitivity was observed and stabilized thereafter like in the case of Example 1.

Figure 5:
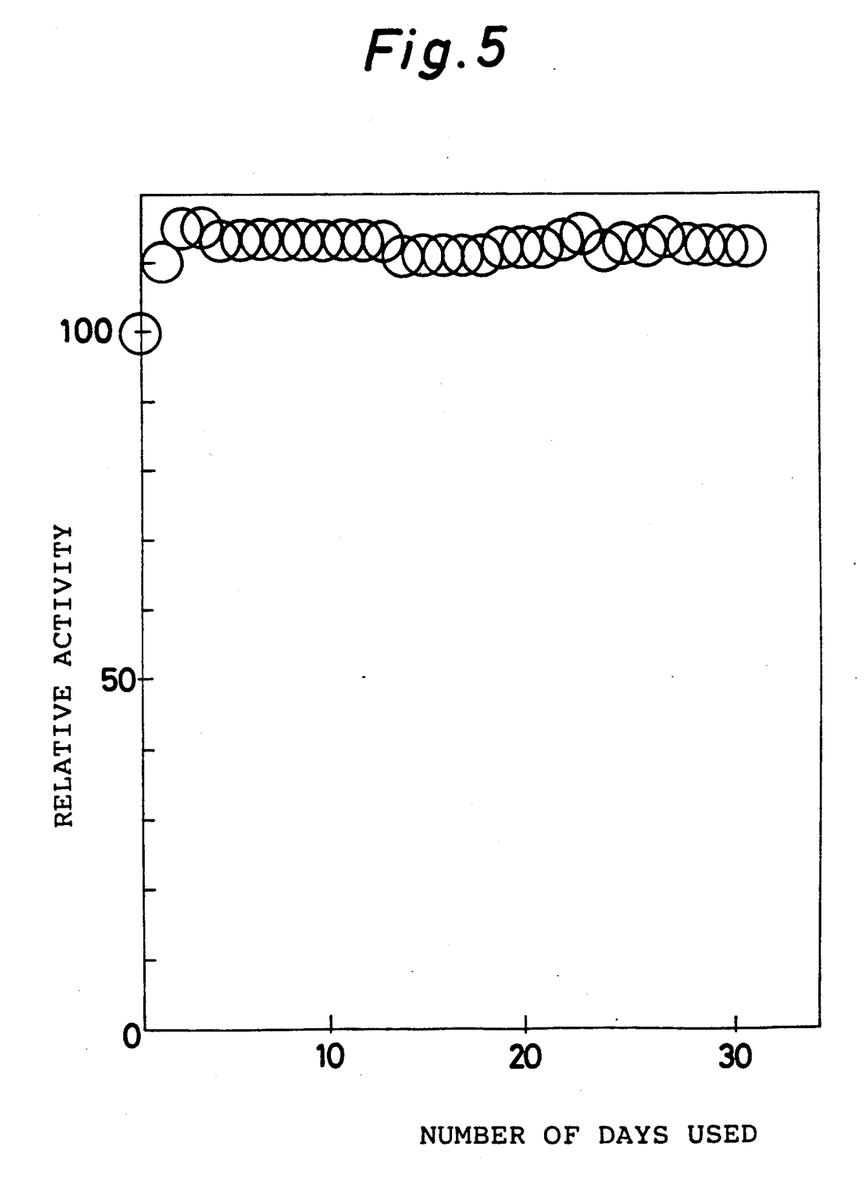
FIG. 5 is a graph showing the results of measurement of Example 3.

As obvious from FIG. 5, the immobilized alcohol oxidase prepared according to the invention was very stable, showing no deterioration of the activity even after a month. This shows that the stability is excellent like in Example 1.

To this apparatus provided with the immobilized enzyme column, ethanol solutions of 100 mM and 1M were alternately injected. In the case of 1M solution, the output value was saturated and could not be determined, but gave no influence on the measurement of 100 mM ethanol solution injected immediately after.

EXAMPLE 4

(1) Preparation of Electrode

The hydrogen peroxide electrode and the column were prepared in the same manner as Example 1.

A glucose measuring electrode was prepared by immobilizing glucose oxidase on the hydrogen peroxide selectively permeable membrane of the hydrogen peroxide electrode same as that used in Example 1. 5 mg/ml of glucose oxidase (derived from *Aspergillus niger*, Type II, supplied by Sigma Co.) and 5 mg/ml of bovine serum albumin (Fraction V, supplied by Sigma Co.) were mixed in the ratio of 1:1, and glutaraldehyde was added to the mixed solution to make the resulting concentration thereof 0.2%. After dropping 5 µl of the mixture on the hydrogen peroxide selectively permeable membrane it was dried at 40° C. for 15 minutes.

(2) Measuring Apparatus

Figure 6:
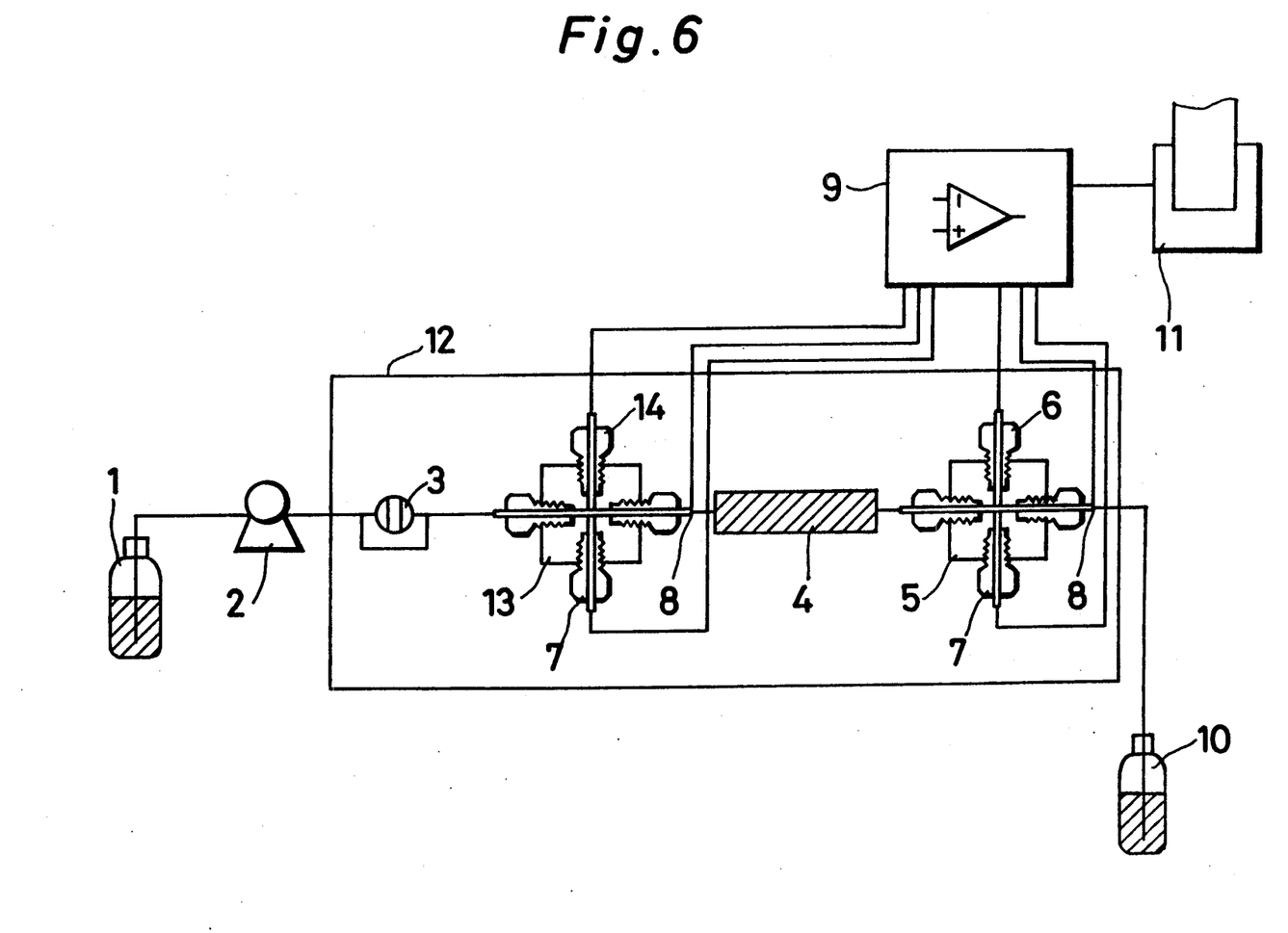
FIG. 6 is a system diagram showing the flow type glucose and alcohol measuring apparatus, an embodiment of the invention used in Example 4.

The glucose measuring electrode 14 mounted on the measuring cell 13 was attached to the flow type measuring apparatus shown in FIG. 2. The configuration was shown in FIG. 6. Other measuring conditions were same as in Example 1.

(3) Measuring Method

Figure 7:
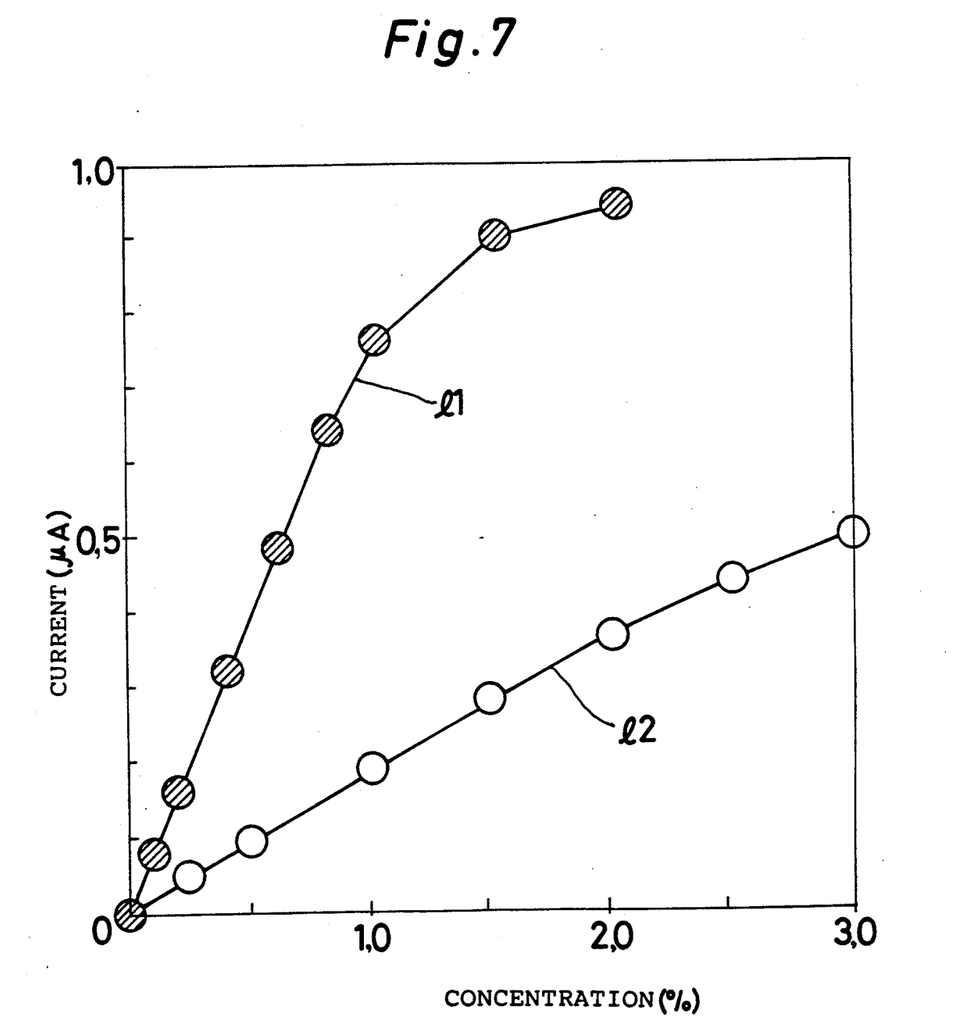
FIG. 7 is a graph showing the calibration curve of glucose (demonstrated by the ⦿) and that of ethanol (demonstrated by the mark o) in Example 4.

The calibration curve when 5 µl of ethanol solution and glucose solution of various concentration were injected from the injector 3 is shown in FIG. 7. The calibration curve 11 represents that of glucose. It is straight line to the range of 0.75% (W/V). The calibration curve 12 represents that of ethanol, and is straight line to the range of 2.0 (V/V). Even when a mixed solution of glucose and alcohol was injected, no interference with each other was observed.

The glucose measuring electrode showed no deterioration of sensitivity for 6 months. Thus, it was found that the use of the apparatus according to the invention provides a high-accuracy and stable glucose and alcohol measuring apparatus.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An immobilized alcohol oxidase produced by at least the following steps of:
   a) bonding an aminosilane coupling agent to the surface of a carrier,
   b) bonding a multifunctional aldehyde to an amino group of said aminosilane coupling agent which is bonded to the surface of said carrier by contacting said carrier with a solution containing the multifunctional aldehyde,
   c) washing said carrier to remove essentially all free multifunctional aldehyde from the carrier, and
   d) bonding an alcohol oxidase to said multifunctional aldehyde which is bonded to said amino group to immobilize a one-molecule thickness of alcohol oxidase on the carrier.

2. The immobilized alcohol oxidase as claimed in claim 1, wherein said carrier possesses hydroxyl groups before step a) is conducted.

3. The immobilized alcohol oxidase as claimed in claim 1, wherein said carrier contains silicate.

4. The immobilized alcohol oxidase as claimed in claim 3, wherein said carrier containing silicate is a diatomaceous earth or a fire brick obtained by high temperature treatment of diatomaceous earth containing material.

5. The immobilized alcohol oxidase as claimed in claim 1, wherein said alcohol oxidase is immobilized on a carrier having a porous surface.

6. A process for preparing an immobilized alcohol oxidase comprising the steps of:
   a) bonding an aminosilane coupling agent to the surface of a carrier,
   b) bonding a multifunctional aldehyde to an amino group of said aminosilane coupling agent which is bonded to the surface of said carrier by contacting said carrier with a solution containing the multifunctional aldehyde,
   c) washing said carrier to remove essentially all free multifunctional aldehyde from the carrier, and
   d) bonding an alcohol oxidase to said multifunctional aldehyde which is bonded to said amino group to immobilize a one-molecule thickness of alcohol oxidase on the carrier.

7. An alcohol measuring apparatus comprising:
   a flow path,
   a column disposed in said flow path filled with a carrier having an immobilized alcohol oxidase,
   a hydrogen peroxide electrode disposed in said flow path downstream of said column, and
   means for supplying a buffer solution to said flow path so that the buffer solution is passed through said column and contacts said hydrogen peroxide electrode, wherein said immobilized alcohol oxidase is produced by at least the following steps of:
   a) bonding an aminosilane coupling agent to the surface of said carrier,
   b) bonding a multifunctional aldehyde to an amino group of said aminosilane coupling agent which is bonded to the surface of said carrier by contacting said carrier with a solution containing the multifunctional aldehyde,
   c) washing said carrier to remove essentially all free multifunctional aldehyde from the carrier, and
   d) bonding an alcohol oxidase to said multifunctional aldehyde which is bonded to said amino group to immobilize a one-molecule thickness of alcohol oxidase on the carrier.

8. The alcohol measuring apparatus as claimed in claim 7, wherein said measuring apparatus additionally comprises an immobilized enzyme electrode for detecting glucose concentration disposed in said flow path upstream of said column or downstream of said hydrogen peroxide electrode.

* * * * *